(12) United States Patent
Kanner

(10) Patent No.: US 6,206,870 B1
(45) Date of Patent: Mar. 27, 2001

(54) CATHETER STYLET HANDLE

(75) Inventor: Rowland W. Kanner, Guntersville, AL (US)

(73) Assignee: Quest Medical, Inc., Allen, TX (US)

( * ) Notice: Subject to any disclaimer, the term of this patent is extended or adjusted under 35 U.S.C. 154(b) by 0 days.

(21) Appl. No.: 09/234,971

(22) Filed: Jan. 21, 1999

(51) Int. Cl.[7] .................................................. A61M 25/00
(52) U.S. Cl. .............................................................. 604/523
(58) Field of Search ............................... 604/95, 164, 523, 604/528, 533; 600/433, 434, 435, 585

(56) References Cited

U.S. PATENT DOCUMENTS

| | | |
|---|---|---|
| 2,164,926 | 7/1939 | Kleine . |
| 3,867,945 | 2/1975 | Long . |
| 4,529,400 | 7/1985 | Scholten . |
| 4,790,825 | 12/1988 | Berstein et al. . |
| 4,808,158 | 2/1989 | Kreuzer et al. . |
| 4,863,430 | 9/1989 | Klyce et al. . |
| 5,226,427 | 7/1993 | Buckberg et al. . |
| 5,344,399 | * | 9/1994 | DeVries ................................. 604/96 |
| 5,360,406 | * | 11/1994 | Boykin et al. ....................... 604/170 |

OTHER PUBLICATIONS

Quest Medical Inc., "Retrograde Cardioplegia Catheter", Jun. 1996.*

* cited by examiner

Primary Examiner—Manuel Mendez
(74) Attorney, Agent, or Firm—Trexler, Bushnell, Giangiorgi, Blackstone & Marr, Ltd.

(57) ABSTRACT

The present invention provides a novel ergonomic handle for a retrograde coronary sinus catheter stylet. The handle is provided at a proximal end of a thin rod. In use, the stylet is inserted into a retrograde cardioplegia catheter. The stylet handle of the present invention extends from the proximal end of the catheter. The handle includes a generally flat, substantially planar body portion having a proximal end, a distal end and an axis extending from the proximal end to the distal end. A first concave pocket is provided at the distal end of the body on one side of the axis and a second concave pocket is provided at the distal end of the body on the opposite side of the axis. Each pocket has a plurality of surfaces against which at least one of the digits of a user may be placed to manipulate the position of the stylet, and thus the catheter. The handle is manipulated in a plane defined by the body so as to manipulate the stylet and the catheter. The body also has a third concave pocket which is proximate to the second pocket. At least one of the user's digits can grip the third pocket.

13 Claims, 4 Drawing Sheets

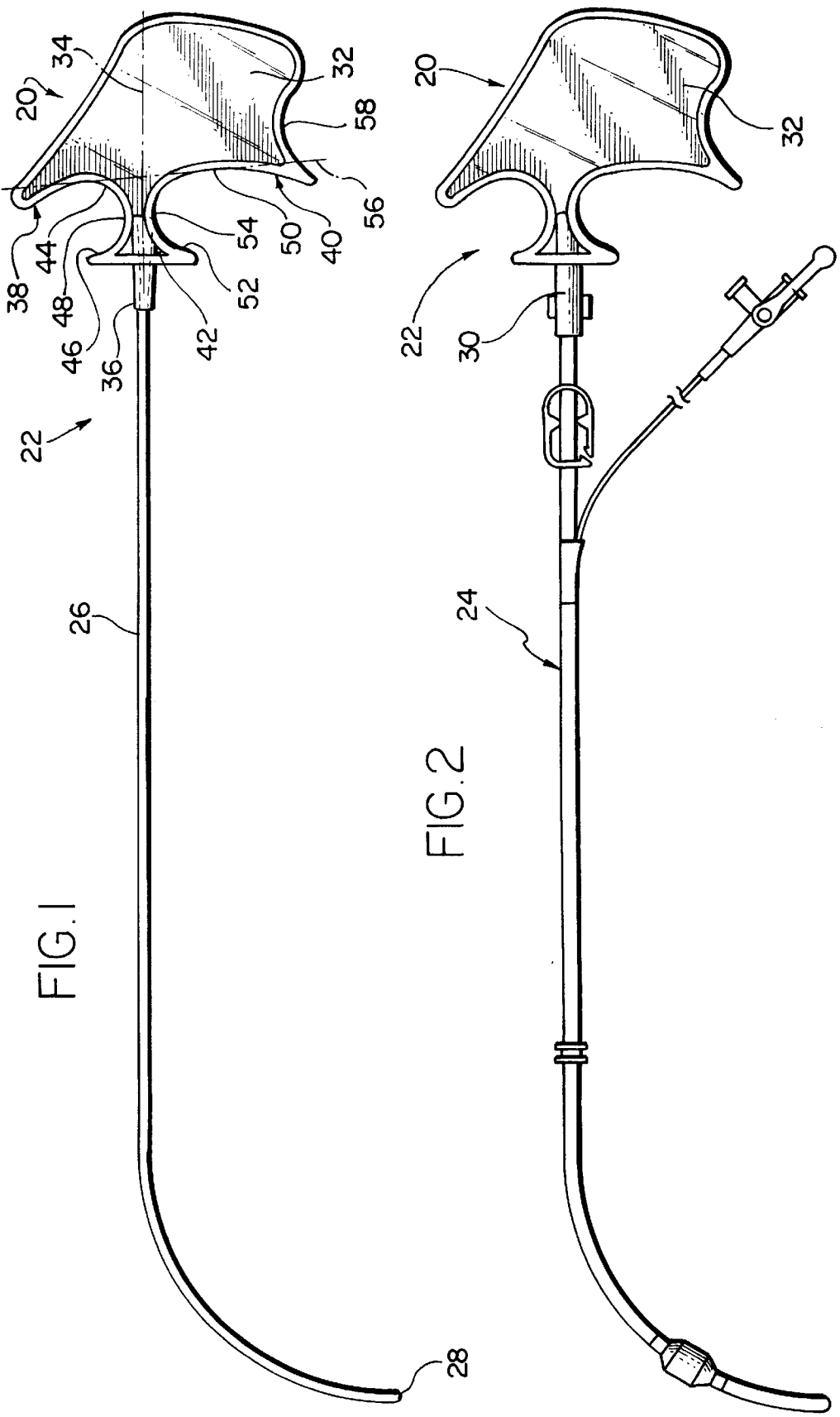

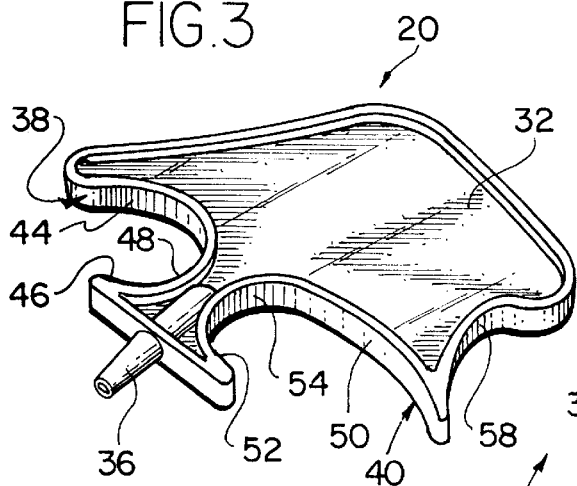
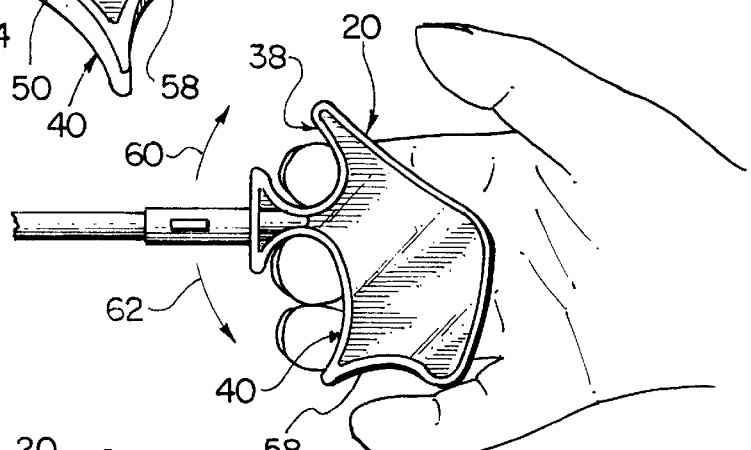
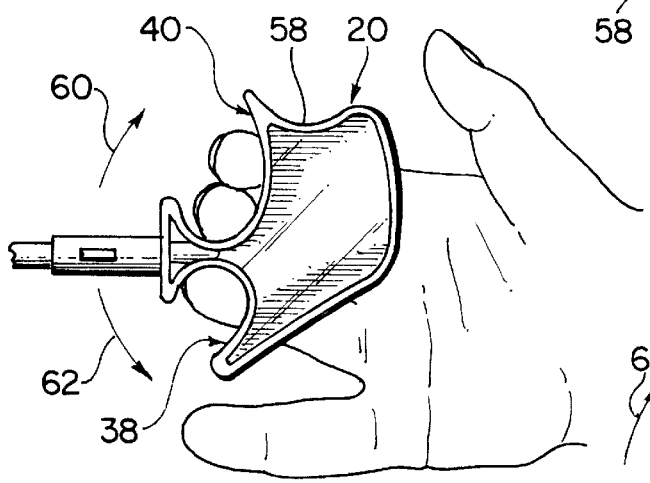
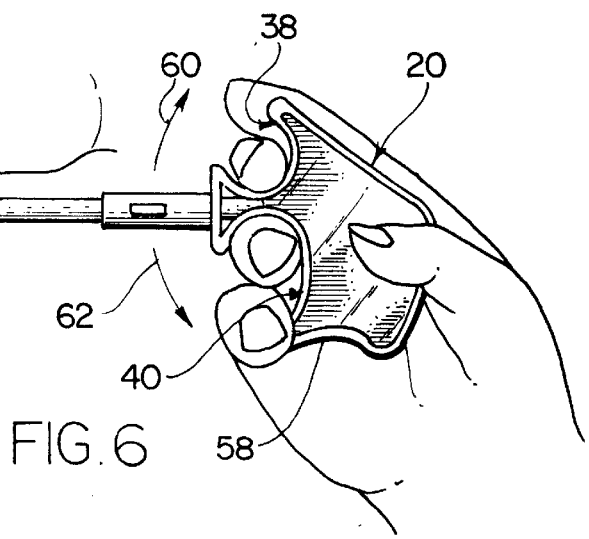

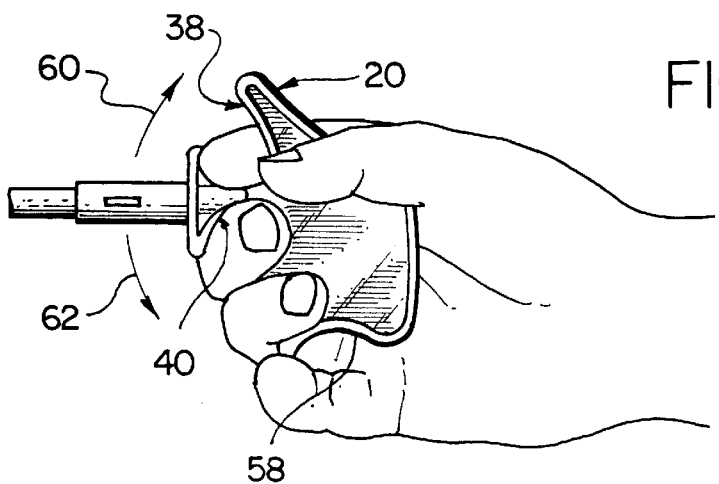
FIG.11
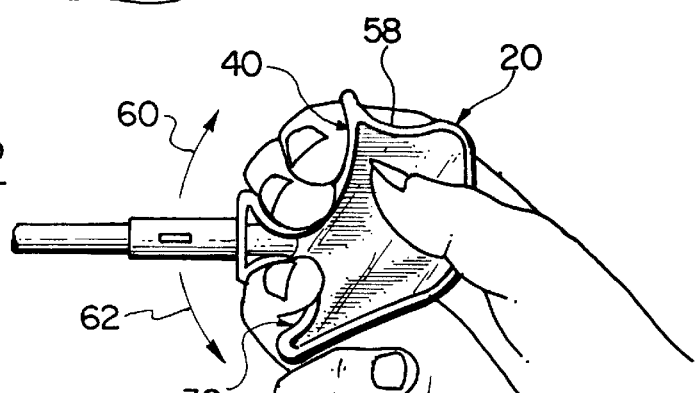
FIG.12
FIG.13
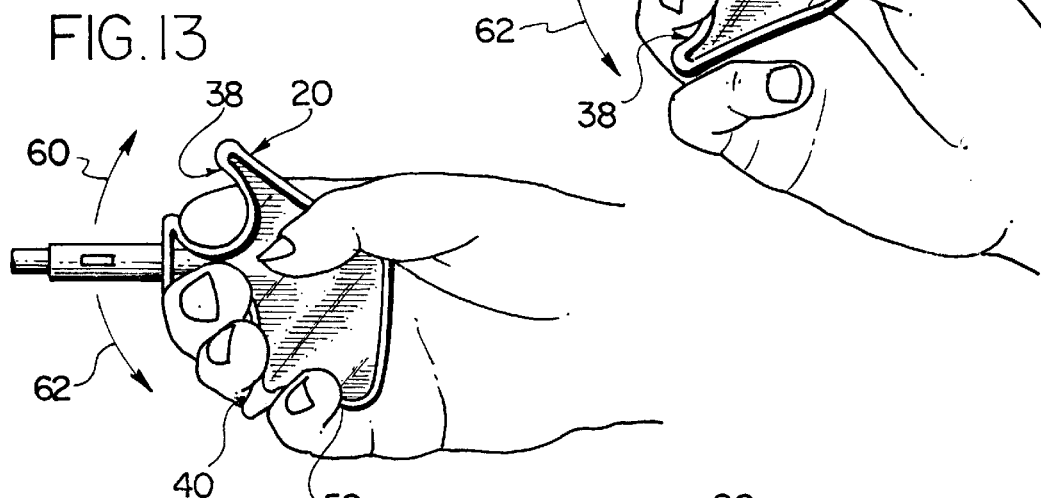
FIG.14
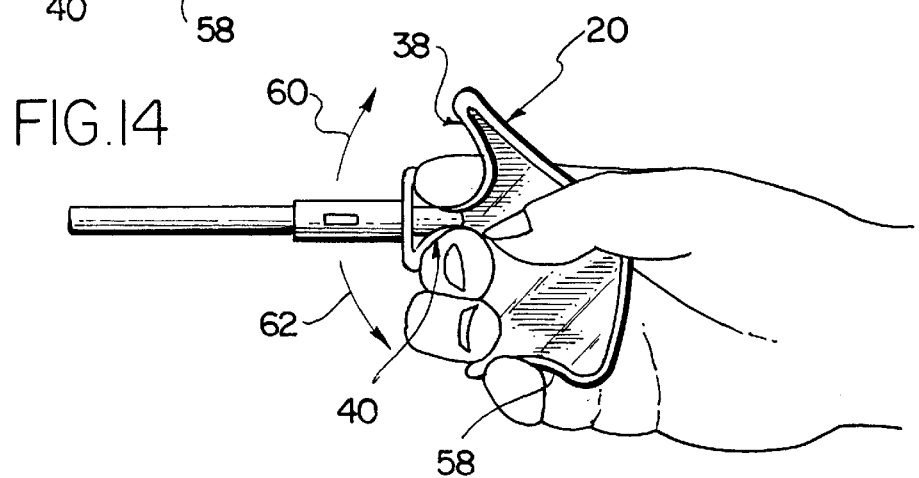

CATHETER STYLET HANDLE

BACKGROUND OF THE INVENTION

This invention is generally directed to a novel ergonomic handle for a catheter stylet useable with a retrograde coronary catheter. More particularly, the invention contemplates a novel handle which can be gripped in a variety of positions by a user, such as a surgeon, for manipulation of the stylet and a cardioplegia catheter mounted upon the stylet to position the catheter within a patient's coronary sinus.

During cardiac surgery, it is essential to have an arrested heart, rather than a beating heart. Cardioplegia solution is delivered to the heart to stop the heart during surgery.

In order to inject the cardioplegia solution into the heart, a cardioplegia catheter is used. A stylet is placed within the catheter and manipulated within the heart by the surgeon to manually place the catheter in the proper position within the coronary sinus. After insertion of the catheter into its proper place within the coronary sinus, the catheter is secured into place, preferably by an inflatable lumen or balloon, and the stylet is withdrawn from the catheter. Cardioplegia solution is then injected into the heart through the catheter to arrest the heart.

One prior art stylet, made by the assignee of the present application, has a flat, generally rectangular handle attached to the end of the rod. Each corner at the distal end of the handle is defined by an arc to form a concave portion of the handle. Each arc that defines each concave portion extends approximately ninety degrees relative to an axis of the handle which is aligned with the rod.

Another prior art stylet has a triangular or pistol-type grip in which the surgeon's thumb or first digit engages a thumb rest at the proximal end of the grip. The proximal thumb rest is specifically provided to reinforce the intended triangular grip. This triangular grip, by virtue of its spaced apart three-point character, almost totally rigidities the handle to a user's hand and forces the employment of wrist action to attain the necessary movement of the curved catheter upon insertion. This form of insertion tends to reduce a user's ability to utilize the more sensitive digits (fingers) for control feedback during insertion. If the catheter is not properly positioned within the heart, cardioplegia delivery is compromised and the patient can suffer serious problems, or at the very least, time is lost and repositioning is required.

The present invention provides a novel, ergonomic handle for a retrograde coronary sinus catheter stylet. Features and advantages of the stylet handle will become apparent upon a reading of the attached specification in combination with a study of the drawings.

OBJECTS AND SUMMARY OF THE INVENTION

A general object of the present invention is to provide a novel ergonomic handle for a retrograde coronary sinus catheter stylet and the method of usage thereof for positioning a cardioplegia catheter into a patient's coronary sinus.

An object of the present invention is to provide a novel handle for a stylet which provides a broad range of grip options for the user.

Another object of the present invention is to provide a novel handle for a stylet which provides a significantly greater additional range of angularity beyond the natural resultant holding angle through digit manipulation than wrist action alone could offer. That is to say, the handle is manipulated primarily with the fingers rather than with wrist action.

Briefly, and in accordance with the foregoing, the present invention discloses a novel ergonomic handle for use in manipulating the position of a retrograde coronary sinus catheter stylet. The handle is provided at a proximal end of a thin curved rod. In use, the stylet is inserted into a retrograde cardioplegia catheter. The stylet handle of the present invention extends from the proximal end of the catheter.

The handle includes a body portion having a proximal end, a distal end and an axis aligned with the rod. In the illustrated embodiment, the handle is substantially planar and generally flat. A first concave recess or pocket is provided at the distal end of the body on one side of the axis and a second concave recess or pocket is provided at the distal end of the body on the opposite side of the axis. Each pocket has a proximal gripping surface, an intermediate gripping surface and a distal abutment surface against which at least one or more of the digits of a user may be placed to manipulate the position of the handle and correspondingly the rod, and thus the catheter. The arc or arcs which defines or define each pocket extends more than ninety degrees relative to said axis such that when the user's digit(s) is placed therein, the digit(s) is/are generally enveloped by the pocket. The handle is pivoted or manipulated in a plane defined by the body of the handle so as to pivot or manipulate the stylet and the attached catheter within the patient's heart for positioning within the coronary sinus. The body also has a third concave pocket which is proximate to the second pocket. At least one of the user's digits can grip the third pocket to provide stability. Most importantly, the manipulation of the body by the user is attained through the use of the user's digits (fingers) which provide sensitive tactile feedback, while wrist action may augment manipulation via the fingers, wrist action is not the primary manner of manipulation of the handle. Also, this manipulation is effected without the employment of a thumb rest, which would tend to rigidify the user's wrist with respect to the stylet handle.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 1 is a side elevational view of a stylet having a handle which incorporates the features of the invention;

FIG. 2 is a side elevational view of the stylet of FIG. 1 inserted into a retrograde cardioplegia catheter;

FIG. 3 is a perspective view of the handle of the present invention;

FIG. 4 illustrates the handle being gripped by a user with a three digit grip with an open hand;

FIG. 5 illustrates the handle being gripped by a user with an inverted three digit pistol grip with an open hand;

FIG. 6 illustrates the handle being gripped by a user with a three digit pistol grip with a closed hand and a pointed second digit;

FIG. 11 illustrates the handle being gripped by a user with a four digit pistol grip with a closed hand;

FIG. 12 illustrates the handle being gripped by a user with an inverted modified three digit pistol grip with a closed hand;

FIG. 13 illustrates the handle being gripped by a user with a modified four digit pistol grip with a closed hand; and FIG. 14 illustrates the handle being gripped by a user with a modified four digit pistol grip with a closed hand.

DETAILED DESCRIPTION OF THE ILLUSTRATED EMBODIMENT

Figure 7:
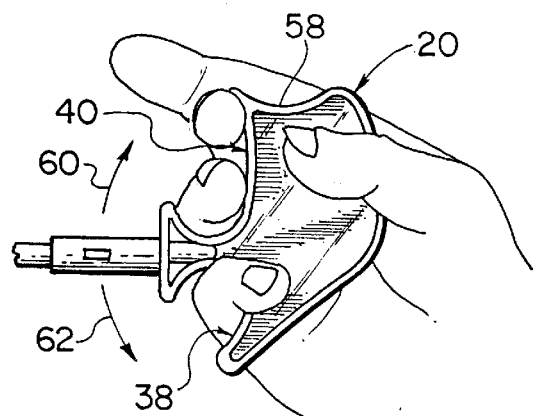
FIG. 7 illustrates the handle being gripped by a user with an inverted three digit pistol grip with a closed hand and a pointed second digit.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein.

The present invention provides a novel ergonomic handle 20 for a stylet 22, FIG. 1, of the general type and kind to be used with a retrograde cardioplegia catheter 24, shown in FIG. 2. The stylet 22 is used to properly position the retrograde cardioplegia catheter 24 in a patient's coronary sinus. As shown in FIG. 1, the handle 20 is provided at a proximal end of a thin rod 26, the handle 20 and the rod 26 forming the stylet 22. The rod 26 can be rigidly formed as a curve or can be malleable to shape the rod 26 into a desired shape. At its distal end, the rod 26 has a rounded tip 28 and a predetermined curve which aids in the proper placement of the stylet 22 within a patient's coronary sinus in the heart. The rounded tip 28 prevents puncturing of the catheter 24 during insertion of the catheter 24 into the patient's heart.

FIG. 2 illustrates the stylet 22 inserted the retrograde cardioplegia catheter 24. The catheter 24 is of conventional design and is therefore not described in detail herein. The catheter 24 includes an inflatable balloon at the distal end thereof and various internal lumens to provide for inflation of the balloon and the delivery of the cardioplegia solution to the patient's heart, once properly positioned in the coronary sinus. The stylet handle 20 of the present invention extends from the proximal end of the catheter 24. A Luer lock 30 is positioned between the stylet handle 20 and the catheter 24, to interconnect the components and provide a sealed connection.

The handle 20 of the stylet 22 is formed from a generally flat or substantially planar body 32 having a proximal end, the end closest to the user, and a distal end, the end farthest away from the user. While the illustrated embodiment employs a substantially flat, generally planar handle 20, it is envisioned that the handle body 32 could be of a more rounded or bulbous shaped, to conform to the user's handle or grip, provided the structure employed for manipulation by the user's digits discussed herein is utilized. An axis 34 through the body 32 extends from the proximal end to the distal end and is in effect an extension of or aligned with the rod 26. The body 32 of the handle 20 has a length, that is the distance from the distal-most point thereof to the proximal-most point thereof, which allows it to fit within a user's hand. The handle 20 is preferably formed from plastic. A tubular, tapered connection portion 36 extends from the distal end of the body 32. The rod 26 extends from the connection portion 36 and is connected thereto by suitable means. When assembled with the catheter 24, the Luer lock 30 on the catheter 24 is frictionally engaged with the connection portion 36.

At the distal end of the body 32, first and second engagement portions or concave recesses or pockets 38, 40 are provided with an extension portion 42 therebetween. The first concave pocket 38 is provided on one side of the axis 34 and the second concave pocket 40 is provided on the opposite side of the axis 34, generally to the plane of the handle body 32. The extension portion 42 is aligned with the axis 34 and the connection portion 36 extends distally therefrom. A user's digits are placed in the first and second concave pockets 38, 40, as described herein, to manipulate the position of the stylet 22 and thus, to manipulate the position of the catheter 24 as described herein.

The first concave pocket 38 has a proximal gripping surface 44 at its proximal end, a generally arcuate distal abutment surface 46 at its distal end, and an intermediate gripping surface 48 connecting the proximal gripping surface 44 and the distal abutment surface 46 together. The proximal gripping surface 44 is generally perpendicular to the axis 34 and has a slightly arcuate shape. The intermediate gripping surface 48 is generally parallel to the axis 34 and has an arcuate shape. The surfaces 44, 46, 48 that define the concave pocket 38 approximate an arc which exceeds ninety degrees such that when a user's digit or digits are placed therein, the digit or digits are enveloped within the pocket 38. It should be noted, that while the surfaces which define the concave pocket 38 are described and illustrated as "arcuate" or "generally arcuate," it is envisioned that a functional design within the scope of this invention could be attained utilizing flat or planar surfaces which generally form an arc.

The second concave pocket 40 has a proximal gripping surface 50 at its proximal end, a generally arcuate distal abutment surface 52 at its distal end, and an intermediate gripping surface 54 connecting the proximal gripping surface 50 and the distal abutment surface 52. The proximal gripping surface 50 is generally perpendicular to the axis 34 and has a slightly arcuate shape. The intermediate gripping surface 54 is generally parallel to the axis 34 and is arcuate. The surfaces 50, 52, 54 that define the concave pocket 40 approximate an arc which exceeds ninety degrees such that when a user's digit or digits are placed therein, the digit or digits are generally enveloped within the pocket 40. It should be noted, that while the surfaces which define the concave pocket 40 are described and illustrated as "arcuate" or "generally arcuate," it is envisioned that a functional design within the scope of this invention could be attained utilizing flat or planar surfaces which generally form an arc.

The proximal gripping surface 44 of the first pocket 38 and the proximal gripping surface 50 of the second pocket 40 are generally aligned with each other along a line shown at 56, such line 56 being generally perpendicular to the axis 34. As shown, the proximal gripping surface 44 of the first pocket 38 is shorter in length than the proximal gripping surface 50 of the second pocket 40.

The body 32 further includes a third concave pocket 58 which is proximal of the first and second pockets 38, 50 and distal of the proximal end of the body 32. The third pocket 58 can be gripped by at least one of the user's digits as described herein. The third pocket 58 is on the same side of the axis 34 as the second pocket 40.

The shape of the proximal end of the handle 20 may be a variety of forms so long as it does not impede movement of the handle 20 as described herein. Preferably, the proximal end of the handle 20 is formed so as to generally conform to a user's hand when the hand is closed around the handle 20, although the user's palm is not used to grip the handle 20 as described herein.

To use the stylet 22, the rod 26 is inserted into the catheter 24 and the Luer lock 30 is slid over and frictionally engages the connection portion 36. The user's digits are used to grip the gripping surfaces in the pockets 38, 40 in one of a variety of positions. Importantly, the proximal end of the handle 20 is not gripped by the user by the user's palm or the user's thumb or first digit. This frees the handle 20 for pivoting or manipulation by the user's digits in the plane of the handle 20, thereby resulting in a better tactile feel because the user is working with his or her digits instead of the whole hand. The handle 20 is securely held for manipulation without employing the thumb or first digit as a gripping member on the proximal end of the handle 20 and relies upon digit support and manipulation, not the wrist, to track the catheter 24 upon insertion into the patient's coronary sinus. This gripping of the handle 20 does not impose a rigid triangular grip upon the user as in the prior art.

A broad range of grip options are made available to the user with the handle 20 of the present invention. Each grip imparts a different catheter 24 angularity with respect to the user's arm/wrist with which to approach his or her patient. There is no one correct grip. Instead, the handle 20 offers a multitude of grip configurations to each user in which the specific condition of use encountered may weigh most heavily in a user's choice. To demonstrate this point, different grips are shown in FIGS. 4–14 to show some of the many possible gripping options. It is to be understood that the positions of the user's digits illustrated in FIGS. 4–14 are merely illustrative, and that other positions may be used. Also, wrist action may be used to augment or supplement digital manipulation.

As shown in FIG. 4, a three digit grip with an open hand is used. In this grip, only the second, third and fourth digits are used to grip the handle 20 of the stylet 22. The user's palm is open and the proximal end of the handle 20 does not contact the user's palm. The second digit is within the first pocket 38 and engages the intermediate gripping surface 48 and the proximal gripping surface 44. The third digit is within the second pocket 40 and engages the intermediate gripping surface 54. Finally, the fourth digit is within the second pocket 40, positioned adjacent the third digit, and engages the proximal gripping surface 50. When the stylet 22 is manipulated by the user, the handle 20 is rotated in the plane of the handle 20. To rotate the stylet 22 and the catheter 24 in the direction of arrow 60, pressure is applied against the proximal gripping surface 44 by the second digit; to rotate the stylet 22 and catheter 24 in the direction of arrow 62, pressure is applied against the proximal gripping surface 50 by the fourth digit. When a thrusting motion is to be employed to move the stylet 22 and the catheter 24 forward, the second and third digits are placed against the respective distal abutment surfaces 46, 52 and forward movement is imparted to the stylet 22 and the catheter 24.

As shown in FIG. 5, an inverted three digit pistol grip with an open hand is used. In this grip, only the second, third and fourth digits are used to grip the handle 20 of the stylet 22. The user's palm is open and the proximal end of the handle 20 does not contact the user's palm. The fourth digit is within the first pocket 38 and engages the intermediate gripping surface 48 and the proximal gripping surface 44. The third digit is within the second pocket 40 and engages the intermediate gripping surface 54. Finally, the second digit is within the second pocket 40, positioned adjacent the third digit, and engages the proximal gripping surface 50. When the stylet 22 is manipulated by the user, the handle 20 is rotated in the plane of the handle 20. To rotate the stylet 22 and the catheter 24 in the direction of arrow 60, pressure is applied against the proximal gripping surface 44 by the second digit; to rotate the stylet 22 and the catheter 24 in the direction of arrow 62, pressure is applied against the proximal gripping surface 50 by the fourth digit. When a thrusting motion is to be employed to move the stylet 22 and the catheter 24 forward, the third and fourth digits are placed against the respective distal abutment surfaces 52, 46 and forward movement is imparted to the stylet 22 and the catheter 24.

As shown in FIG. 6, a three digit pistol grip with a closed hand and a pointed second digit is used. In this grip, only the third, fourth and fifth digits are used to grip the handle 20 of the stylet 22. The user's palm is closed such that the first digit overlaps the handle 20, but user's palm does not press against the proximal end of the handle 20 and the first digit does not press against the handle 20. The third digit is within the first pocket 38 and engages the intermediate gripping surface 48 and the proximal gripping surface 44. The second digit is pointed and is proximate to the third digit, but is not used to move the handle 20. The fourth digit is within the second pocket 40 and engages the intermediate gripping surface 54. Finally, the fifth digit is within the second pocket 40, positioned adjacent the fourth digit, and engages the proximal gripping surface 50. When the stylet 22 is manipulated by the user, the handle 20 is rotated in the plane of the handle 20. To rotate the stylet 22 and the catheter 24 in the direction of arrow 60, pressure is applied against the proximal gripping surface 44 by the third digit; to rotate the stylet 22 in the direction of arrow 62, pressure is applied against the proximal gripping surface 50 by the fifth digit. When a thrusting motion is to be employed to move the stylet 22 and the catheter 24 forward, the third and fourth digits are placed against the respective distal abutment surfaces 46, 52 and forward movement is imparted to the stylet 22 and catheter.

As shown in FIG. 7, an inverted three digit pistol grip with a closed hand and a pointed second digit is used. In this grip, only the third, fourth and fifth digits are used to grip the handle 20 of the stylet 22. The user's palm is closed such that the first digit overlaps the handle 20, but user's palm does not press against the proximal end of the handle 20 and the first digit does not press against the handle 20. The fifth digit is within the first pocket 38 and engages the intermediate gripping surface 48 and the proximal gripping surface 44. The fourth digit is within the second pocket 40 and engages the intermediate gripping surface 54. The third digit is within the second pocket 40, positioned adjacent the fourth digit, and engages the proximal gripping surface 50. The second digit is pointed and is proximate to the third digit, but is not used to move the handle 20. When the stylet 22 is manipulated by the user, the handle 20 is rotated in the plane of the handle 20. To rotate the stylet 22 and the catheter 24 in the direction of arrow 60, pressure is applied against the proximal gripping surface 50 by the third digit; to rotate the stylet 22 and catheter 24 in the direction of arrow 62, pressure is applied against the proximal gripping surface 44 by the fifth digit. When a thrusting motion is to be employed to move the stylet 22 and the catheter 24 forward, the fourth and fifth digits are placed against the respective distal abutment surfaces 52, 46 and forward movement is imparted to the stylet 22 and the catheter 24.

Figure 8:
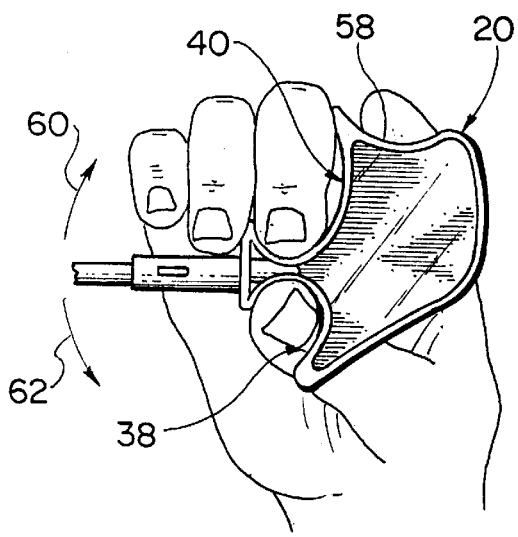
FIG. 8 illustrates the handle being gripped by a user with a flat handed side grip.

As shown in FIG. 8, a flat handed side grip is used. In this grip, only the first, second and third digits are used. The first digit is positioned in the first pocket 38 and engages against the intermediate gripping surface 48. The third digit is positioned in the second pocket 40 and engages against the intermediate gripping surface 54. The second digit is positioned in the third pocket 58 and is used to rotate the stylet 22 and the catheter 24 in the directions of the arrows 60, 62. When a thrusting motion is to be employed to move the stylet 22 and the catheter 24 forward, the first and third digits are placed against the respective distal abutment surfaces 46, 52 and forward movement is imparted to the stylet 22 and the catheter 24. The second digit is also used to impart a thrusting force on the stylet 22 and the catheter 24.

Figure 9:
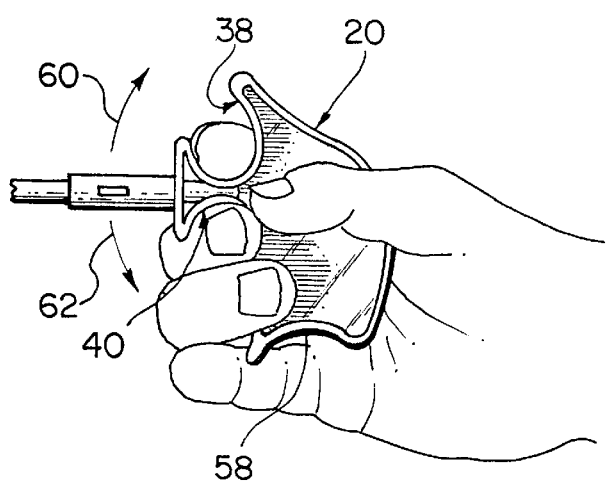
FIG. 9 illustrates the handle being gripped by a user with a three digit pistol grip with a closed hand.

As shown in FIG. 9, a three digit pistol grip with a closed hand is used. In this grip, only the second, third and fourth digits are used to grip the handle 20 of the stylet 22. The user's palm is closed such that the first digit overlaps the handle 20, but user's palm does not press against the proximal end of the handle 20 and the first digit does not press against the handle 20. The second digit is within the first pocket 38 and engages the intermediate gripping surface 48 and the proximal gripping surface 44. The third digit is within the second pocket 40 and engages the intermediate gripping surface 54. Finally, the fourth digit is within the second pocket 30, positioned adjacent the third digit, and engages the proximal gripping surface 50. When the stylet 22 is manipulated by the user, the handle 20 is rotated in the plane of the handle 20. To rotate the stylet 22 and the catheter 24 in the direction of arrow 60, pressure is applied against the proximal gripping surface 44 by the second digit; to rotate the stylet 22 and the catheter 24 in the direction of arrow 62, pressure is applied against the proximal gripping surface 50 by the fourth digit. When a thrusting motion is to be employed to move the stylet 22 and the catheter 24 forward, the second and third digits are placed against the respective distal abutment surfaces 46, 52 and forward movement is imparted to the stylet 22 and the catheter 24.

Figure 10:
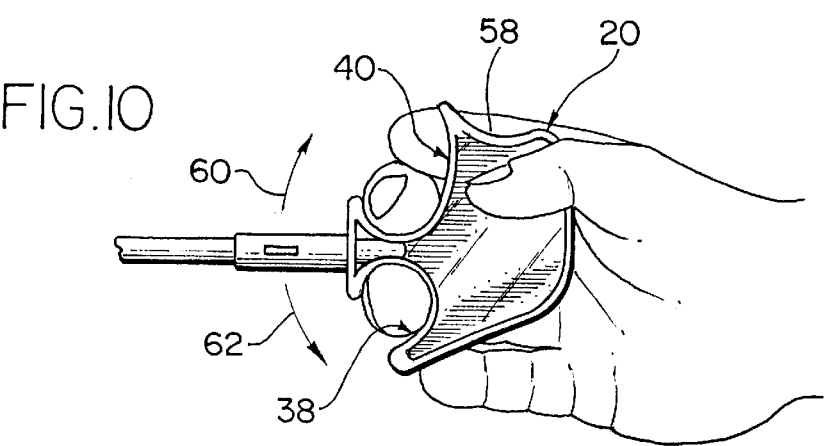
FIG. 10 illustrates the handle being gripped by a user with an inverted modified three digit pistol grip with a closed hand.

As shown in FIG. 10, an inverted modified three digit pistol grip with a closed hand is used. In this grip, only the second, third and fourth digits are used to grip the handle 20 of the stylet 22. The user's palm is closed such that the first digit overlaps the handle 20, but user's palm does not press against the proximal end of the handle 20 and the first digit does not press against the handle 20. The fourth digit is within the first pocket 38 and engages the intermediate gripping surface 48 and the proximal gripping surface 44. The third digit is within the second pocket 40 and engages the intermediate gripping surface 54. Finally, the second digit is within the second pocket 40, positioned adjacent the third digit, and engages the proximal gripping surface 50. When the stylet 22 is manipulated by the user, the handle 20 is rotated in the plane of the handle 20. To rotate the stylet 22 and the catheter 24 in the direction of arrow 60, pressure is applied against the proximal gripping surface 50 by the second digit; to rotate the stylet 22 and the catheter 24 in the direction of arrow 62, pressure is applied against the proximal gripping surface 44 by the fourth digit. When a thrusting motion is to be employed to move the stylet 22 and the catheter 24 forward, the third and fourth digits are placed against the respective distal abutment surfaces 52, 46 and forward movement is imparted to the stylet 22 and the catheter 24.

As shown in FIG. 11, a four digit pistol grip with a closed hand is used. In this grip, only the second, third, fourth and fifth digits are used to grip the handle 20. The user's palm is closed such that the first digit overlaps the handle 20, but user's palm does not press against the proximal end of the handle 20 and the first digit does not press against the handle 20. The second digit is within the first pocket 38 and engages the intermediate gripping surface 48 and the proximal gripping surface 44. The third and fourth digits are within the second pocket 40 and engage the proximal gripping surface 50. Finally, the fifth digit engages the distal end of the third pocket 58. When the stylet 22 is manipulated by the user, the handle 20 is rotated in the plane of the handle 20. To rotate the stylet 22 and the catheter 24 in the direction of arrow 60, pressure is applied against the proximal gripping surface 44 by the second digit; to rotate the stylet 22 and the catheter 24 in the direction of arrow 62, pressure is applied against the proximal gripping surface 50 by the fourth digit. The fifth digit is used to stabilize the handle 20 during rotation. When a thrusting motion is to be employed to move the stylet 22 and the catheter 24 forward, the second and third digits are placed against the respective distal abutment surfaces 46, 52 and forward movement is imparted to the stylet 22 and the catheter 24. The fifth digit is also used to impart a thrusting force on the stylet 22.

As shown in FIG. 12, an inverted modified three digit pistol grip with a closed hand is used. In this grip, only the second, third and fourth digits are used to grip the handle 20 of the stylet 22. The user's palm is closed such that the first digit overlaps the handle 20, but user's palm does not press against the proximal end of the handle 20 and the first digit does not press against the handle 20. The fourth digit is within the first pocket 38 and engages the intermediate gripping surface 48 and the proximal gripping surface 44. The third digit is within the second pocket 40 and engages the intermediate gripping surface 54. Finally, the second digit is within the second pocket 40, positioned adjacent the third digit, and engages the proximal gripping surface 50. When the stylet 22 is manipulated by the user, the handle 20 is rotated in the plane of the handle 20. To rotate the stylet 22 and the catheter 24 in the direction of arrow 60, pressure is applied against the proximal gripping surface 50 by the second digit; to rotate the stylet 22 and the catheter 24 in the direction of arrow 62, pressure is applied against the proximal gripping surface 44 by the fourth digit. When a thrusting motion is to be employed to move the stylet 22 and the catheter 24 forward, the third and fourth digits are placed against the respective distal abutment surfaces 52, 46 and forward movement is imparted to the stylet 22 and the catheter 24.

As shown in FIG. 13, a modified four digit pistol grip with a closed hand is used. In this grip, only the second, third, fourth and fifth digits are used to grip the handle 20. The user's palm is closed such that the first digit overlaps the handle 20, but user's palm does not press against the proximal end of the handle 20 and the first digit does not press against the handle 20. The second digit is within the first pocket 38 and engages the intermediate gripping surface 48 and the proximal gripping surface 44. The third digit is within the second pocket 40 and engages the intermediate gripping surface 54. The fourth digit is within the second pocket 40, proximate to the third digit, and engages the proximal gripping surface 50. Finally, the fifth digit engages the third pocket 58. When the stylet 22 is manipulated by the user, the handle 20 is rotated in the plane of the handle 20. To rotate the stylet 22 and the catheter 24 in the direction of arrow 60, pressure is applied against the proximal gripping surface 44 by the second digit; to rotate the stylet 22 and the catheter 24 in the direction of arrow 62, pressure is applied against the proximal gripping surface 50 by the fourth digit. The fifth digit is used to stabilize the handle 20 during rotation. When a thrusting motion is to be employed to move the stylet 22 and the catheter 24 forward, the second and third digits are placed against the respective distal abutment surfaces 46, 52 and forward movement is imparted to the stylet 22 and the catheter 24. The fifth digit is also used to impart a thrusting force on the stylet 22.

As shown in FIG. 14, a modified four digit pistol grip with a closed hand is used. In this grip, only the second, third, fourth and fifth digits are used to grip the handle 20. The user's palm is closed such that the first digit overlaps the handle 20, but user's palm does not press against the proximal end of the handle 20 and the first digit does not press against the handle 20. The second digit is within the first pocket 38 and engages the intermediate gripping surface 48 and the proximal gripping surface 44. The third digit is within the second pocket 40 and engages the intermediate gripping surface 54. The fourth digit is within the second pocket 40, proximate to the third digit, and engages the proximal gripping surface 50. Finally, the fifth digit engages the third pocket 58. When the stylet 22 is manipulated by the user, the handle 20 is rotated in the plane of the handle 20. To rotate the stylet 22 and the catheter 24 in the direction of arrow 60, pressure is applied against the proximal gripping surface 44 by the second digit; to rotate the stylet 22 and the catheter 24 in the direction of arrow 62, pressure is applied against the proximal gripping surface 50 by the fourth digit. The fifth digit is used to stabilize the handle 20 during rotation. When a thrusting motion is to be employed to move the stylet 22 and the catheter 24 forward, the second and third digits are placed against the respective distal abutment surfaces 46, 52 and forward movement is imparted to the stylet 22 and the catheter 24. The fifth digit is also used to impart a thrusting force on the stylet 22.

In all of FIGS. 4–14, the natural resultant angle of the axis for each form versus the user's arm/wrist angle should be noted. The positions as shown in FIGS. 4–7 and 9–14 provide a significantly greater additional range of angularity beyond the natural resultant holding angle through digit manipulation than wrist action alone could offer. This range can be compounded and thus even further extended through flexing of the wrist. In addition, the user may desire to only place the fingertips in the pockets 38, 40, 58 for tactile feel.

As will be appreciated in these grips, because the proximal gripping surfaces 38, 40 are generally perpendicular to the axis 34 of the body 32, no one digit leads the other. Also, rotation of the handle 20 about one digit through the "trigger pulling" motion of digit(s) oppositely disposed allows tracking of the curved catheter tip during catheter 24 insertion.

It will be appreciated that the handle 20 of the present invention can be used with either the right hand or left hand of the user, employing any number of grips, depending on the user's preference and the circumstances of the surgery.

Moreover, it will be appreciated that a polygonal shape approximating the arcuate surfaces 44, 46, 48, 50, 52, 54 can be used.

Finally, it will be appreciated that the surfaces 44, 46, 48, 50, 52, 54 and the surface of pocket 58 could be notched, serrated, dimpled, stippled or the like to provide for a better gripping surface.

While a preferred embodiment of the present invention is shown and described, it is envisioned that those skilled in the art may devise various modifications of the present invention without departing from the spirit and scope of the appended claims.

The invention claimed is:

1. A handle for a stylet comprising: a body portion having a proximal end, a distal end and an axis extending from said proximal end to said distal end through said body, said distal end having a first recess on one side of said axis in which at least one of a user's digits may be placed, and a second recess at said distal end on the opposite side of said axis in which at least one of the user's other digits may be placed, said body portion substantially enveloping at least one of the user's digits within at least one of said first recess or said second recess, wherein manipulation of said body portion about said axis is solely accomplished by using the digits of the user's without employment of a force on said proximal end of said body portion and wherein insertion forces of said body portion along said axis into a vessel and withdrawal forces of said body portion along said axis from the vessel is solely accomplished by using the digits of the user's without employment of a force on said proximal end of said body portion.

2. A handle as defined in claim 1, wherein a proximal surface of said first recess is generally perpendicular to said axis and can be gripped by at least one of the user's digits and a proximal surface of said second recess is generally perpendicular to said axis and can be gripped by at least one of the user's digits.

3. A handle as defined in claim 2, wherein said proximal surface of said first recess and said proximal surface of said second recess are generally aligned with each other along a line generally perpendicular to said axis.

4. A handle as defined in claim 2, wherein said proximal surface of said second recess is longer in length than said proximal surface of said first recess.

5. A handle as defined in claim 2, wherein said body portion is generally flat and substantially planar.

6. A handle as defined in claim 1, wherein a proximal surface of at least one of said first recess and said second recess is generally perpendicular to the axis and can be gripped by at least one of the user's digits.

7. A handle as defined in claim 1, wherein said body portion further includes attachment means for attaching a rod thereto.

8. A handle as defined in claim 1, wherein said body portion is generally flat and substantially planar.

9. A stylet comprising: a rod; a handle attached to said rod, said handle comprising a body portion having a proximal end and a distal end, an axis aligned with said rod, and at least two surfaces, each said surface being capable of being gripped by at least one of a user's digits, at least one of the user's digits being substantially enveloped by at least one of said surfaces, said surfaces opposing each other about said axis to provide for control of rod insertion, manipulation and withdrawal control forces solely by at least two of the user's digits, without employment of a force on said proximal end of said body portion.

10. A stylet as defined by claim 9 wherein said body portion is flat.

11. A method of using a stylet comprising the steps of:
providing a stylet having a handle and a rod attached to said handle at a distal end thereof, said handle including a body portion having a proximal end, a distal end and an axis extending from said proximal end to said distal end through said body, said distal end having a first recess on one side of said axis, and a second recess on the opposite side of said axis, said body portion substantially enveloping at least one of a user's digits within at least one of said first recess or said second recess;

inserting said rod into a catheter such that said handle extends from the catheter;

gripping said first recess with at least one of the user's digits;

gripping said second recess with at least one of the user's other digits;

solely using the user's digits to manipulate said handle to control rod insertion;

solely using the user's digits to manipulate said handle in a plane defined by said body portion so as to manipulate said rod and the catheter; and solely using the user's digits to manipulate said handle to control rod withdrawal control forces.

12. A method as defined in claim 11, wherein said body portion further has a third recess proximal of said first and second recesses and distal of said proximal end of said body portion, and further including the step of gripping said third recess with at least one of the user's digits prior to said step of manipulating said handle in a plane defined by said body portion so as to manipulate said rod and the catheter.

13. A method as defined in claim 11, further including the step of removing said stylet from the catheter.

* * * * *